US006689151B2

(12) United States Patent
Becker et al.

(10) Patent No.: US 6,689,151 B2
(45) Date of Patent: Feb. 10, 2004

(54) VARIABLE WALL THICKNESS FOR DELIVERY SHEATH HOUSING

(75) Inventors: Wayne A. Becker, Elk River, MN (US); Frank A. Musbach, St. Paul, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 111 days.

(21) Appl. No.: 09/770,030

(22) Filed: Jan. 25, 2001

(65) Prior Publication Data

US 2002/0099407 A1 Jul. 25, 2002

(51) Int. Cl.[7] ............................................. A61M 29/00
(52) U.S. Cl. ...................................... 606/200; 606/194
(58) Field of Search ................................ 606/200, 159, 606/108, 198, 192, 194, 195; 604/96.01, 500, 22, 104

(56) References Cited

U.S. PATENT DOCUMENTS

| | | | |
|---|---|---|---|
| 3,472,230 A | 10/1969 | Fogarty | 128/328 |
| 3,592,186 A | 7/1971 | Oster | 128/2 R |
| 3,683,904 A | 8/1972 | Forster | 128/127 |
| 3,889,657 A | 6/1975 | Baumgarten | 128/2 |
| 3,952,747 A | 4/1976 | Kimmell, Jr. | 128/303 R |
| 3,996,938 A | 12/1976 | Clark, III | 128/348 |
| 4,046,150 A | 9/1977 | Schwartz et al. | 128/328 |
| 4,425,908 A | 1/1984 | Simon | 128/1 |
| 4,447,227 A | 5/1984 | Kotsanis | 604/95 |
| 4,580,568 A | 4/1986 | Gianturco | 128/345 |

(List continued on next page.)

FOREIGN PATENT DOCUMENTS

| | | | |
|---|---|---|---|
| DE | 28 21 048 | 7/1980 | A61B/17/22 |
| DE | 34 17 738 | 11/1985 | A61M/1/34 |
| DE | 40 30 998 A1 | 10/1990 | A61F/2/01 |
| DE | 199 16 162 | 10/2000 | |
| EP | 0 200 688 | 11/1986 | A61B/17/22 |
| EP | 0 293 605 A1 | 12/1988 | A61F/2/02 |
| EP | 0 411 118 A1 | 2/1991 | A61M/25/00 |
| EP | 0 427 429 A2 | 5/1991 | A61M/25/10 |
| EP | 0 437 121 B1 | 7/1991 | A61F/2/02 |
| EP | 0 472 334 A1 | 2/1992 | A61F/2/02 |

(List continued on next page.)

OTHER PUBLICATIONS

"Atherosclerotic Disease of the Aortic Arch as a Risk Factor of Recurrent Ischemic Stroke," *The New England Journal of Medicine*, pp. 1216–1221 (May 1996).

(List continued on next page.)

*Primary Examiner*—John J. Calvert
*Assistant Examiner*—Alissa L. Hoey
(74) *Attorney, Agent, or Firm*—Crompton, Seager & Tufte, LLC

(57) ABSTRACT

A delivery sheath for an intravascular emboli capturing filter including an elongate tube having a distal region having a reduced thickness distal wall region. The delivery sheath, according to the present invention, can have a thinner, softer, distal most portion for superior and more benign interaction with vessel interior walls. The present invention includes an intravascular emboli filter system including an elongate shaft having a distal region, an expandable emboli filter operably coupled to the elongate shaft distal region, and an elongate sheath having a lumen therethrough disposed over the elongate shaft. The elongate sheath can have a distally decreasing outside diameter taper or reduced wall thickness region having improved atraumatic characteristics.

5 Claims, 2 Drawing Sheets

U.S. PATENT DOCUMENTS

| | | | |
|---|---|---|---|
| 4,590,938 A | 5/1986 | Segura et al. | 128/328 |
| 4,619,246 A | 10/1986 | Molgaard-Nielsen et al. | 128/1 |
| 4,631,052 A | 12/1986 | Kensey | 604/22 |
| 4,643,184 A | 2/1987 | Mobin-Uddin | 128/303 |
| 4,650,466 A | 3/1987 | Luther | 604/95 |
| 4,662,885 A | 5/1987 | DiPisa, Jr. | 623/12 |
| 4,705,517 A | 11/1987 | DiPisa, Jr. | 623/12 |
| 4,706,671 A | 11/1987 | Weinrib | 128/348.1 |
| 4,723,549 A | 2/1988 | Wholey et al. | 128/344 |
| 4,728,319 A | 3/1988 | Masch | 604/22 |
| 4,733,665 A | 3/1988 | Palmaz | 128/343 |
| 4,775,371 A * | 10/1988 | Mueller, Jr. | 604/280 |
| 4,790,812 A | 12/1988 | Hawkins, Jr. et al. | 604/22 |
| 4,790,813 A | 12/1988 | Kensey | 604/22 |
| 4,794,928 A | 1/1989 | Kletschka | 128/344 |
| 4,794,931 A | 1/1989 | Yock | 128/660.03 |
| 4,800,882 A | 1/1989 | Gianturco | 128/343 |
| 4,807,626 A | 2/1989 | McGirr | 128/328 |
| 4,842,579 A | 6/1989 | Shiber | 606/22 |
| 4,857,045 A | 8/1989 | Rydell | 604/22 |
| 4,857,046 A | 8/1989 | Stevens et al. | 604/22 |
| 4,867,157 A | 9/1989 | McGurk-Burleson et al. | 128/305 |
| 4,873,978 A | 10/1989 | Ginsburg | 128/345 |
| 4,898,575 A | 2/1990 | Fischell et al. | 604/22 |
| 4,907,336 A | 3/1990 | Gianturco | 29/515 |
| 4,921,478 A | 5/1990 | Solano et al. | 604/53 |
| 4,921,484 A | 5/1990 | Hillstead | 604/104 |
| 4,926,858 A | 5/1990 | Gifford, III et al. | 606/159 |
| 4,950,277 A | 8/1990 | Farr | 606/159 |
| 4,955,895 A | 9/1990 | Sugiyama et al. | 606/194 |
| 4,957,482 A | 9/1990 | Shiber | 604/22 |
| 4,969,891 A | 11/1990 | Gewertz | 606/200 |
| 4,979,951 A | 12/1990 | Simpson | 606/159 |
| 4,986,807 A | 1/1991 | Farr | 604/22 |
| 4,998,539 A | 3/1991 | Delsanti | 128/898 |
| 5,002,560 A | 3/1991 | Machold et al. | 606/198 |
| RE33,569 E | 4/1991 | Gifford, III et al. | 606/159 |
| 5,007,896 A | 4/1991 | Shiber | 604/22 |
| 5,007,917 A | 4/1991 | Evans | 606/170 |
| 5,011,488 A | 4/1991 | Ginsburg | 606/159 |
| 5,019,088 A | 5/1991 | Farr | 606/159 |
| 5,041,126 A | 8/1991 | Gianturco | 606/195 |
| 5,053,008 A | 10/1991 | Bajaj | 604/104 |
| 5,053,044 A | 10/1991 | Mueller et al. | 606/159 |
| 5,071,407 A | 12/1991 | Termin et al. | 604/104 |
| 5,071,425 A | 12/1991 | Gifford, III et al. | 606/159 |
| 5,085,662 A | 2/1992 | Willard | 606/159 |
| 5,087,265 A | 2/1992 | Summers | 606/159 |
| 5,100,423 A | 3/1992 | Fearnot | 606/15 |
| 5,100,424 A | 3/1992 | Jang et al. | 606/159 |
| 5,100,425 A | 3/1992 | Fischell et al. | 606/159 |
| 5,102,415 A | 4/1992 | Guenther et al. | 606/159 |
| 5,104,399 A | 4/1992 | Lazarus | 623/1 |
| 5,108,419 A | 4/1992 | Reger et al. | 606/200 |
| 5,133,733 A | 7/1992 | Rasmussen et al. | 606/200 |
| 5,135,531 A | 8/1992 | Shiber | 606/159 |
| 5,152,771 A | 10/1992 | Sabbaghian et al. | 606/159 |
| 5,152,777 A | 10/1992 | Goldberg et al. | 606/200 |
| 5,160,342 A | 11/1992 | Reger et al. | 606/200 |
| 5,171,233 A | 12/1992 | Amplatz et al. | 604/281 |
| 5,190,546 A | 3/1993 | Jervis | 606/78 |
| 5,195,955 A | 3/1993 | Don Michael | 604/22 |
| 5,209,727 A * | 5/1993 | Radisch, Jr. et al. | 604/96 |
| 5,224,953 A | 7/1993 | Morgentaler | 606/192 |
| 5,306,286 A | 4/1994 | Stack et al. | 606/198 |
| 5,314,444 A | 5/1994 | Gianturco | 606/195 |
| 5,314,472 A | 5/1994 | Fontaine | 623/12 |
| 5,318,576 A | 6/1994 | Plassche, Jr. et al. | 606/159 |
| 5,329,942 A | 7/1994 | Gunther et al. | 128/898 |
| 5,330,484 A | 7/1994 | Gunther | 606/128 |
| 5,330,500 A | 7/1994 | Song | 606/198 |
| 5,350,398 A | 9/1994 | Pavcnik et al. | 606/200 |
| 5,354,310 A | 10/1994 | Garnic et al. | 606/198 |
| 5,356,423 A | 10/1994 | Tihon et al. | 606/194 |
| 5,366,464 A | 11/1994 | Belknap | 606/159 |
| 5,366,473 A | 11/1994 | Winston et al. | 606/198 |
| 5,370,657 A | 12/1994 | Irie | 606/200 |
| 5,370,683 A | 12/1994 | Fontaine | 623/1 |
| 5,376,100 A | 12/1994 | Lefebvre | 606/180 |
| 5,383,887 A | 1/1995 | Nadal | 606/200 |
| 5,383,892 A | 1/1995 | Cardon et al. | 606/198 |
| 5,383,926 A | 1/1995 | Lock et al. | 623/1 |
| 5,387,235 A | 2/1995 | Chuter | 623/1 |
| 5,395,349 A | 3/1995 | Quiachon et al. | 604/248 |
| 5,397,345 A | 3/1995 | Lazerus | 623/1 |
| 5,404,887 A * | 4/1995 | Prather | 128/772 |
| 5,405,377 A | 4/1995 | Cragg | 623/1 |
| 5,409,454 A | 4/1995 | Fischell et al. | 604/22 |
| 5,415,630 A | 5/1995 | Gory et al. | 604/53 |
| 5,419,774 A | 5/1995 | Willard et al. | 604/22 |
| 5,421,832 A | 6/1995 | Lefebvre | 604/53 |
| 5,423,742 A | 6/1995 | Theron | 604/28 |
| 5,423,885 A | 6/1995 | Williams | 623/1 |
| 5,425,765 A | 6/1995 | Tiefenbrun et al. | 623/12 |
| 5,443,498 A | 8/1995 | Fontaine | 623/1 |
| 5,449,372 A | 9/1995 | Schmaltz et al. | 606/198 |
| 5,456,667 A | 10/1995 | Ham et al. | 604/107 |
| 5,462,529 A | 10/1995 | Simpson et al. | 604/101 |
| 5,476,104 A | 12/1995 | Sheahon | 128/757 |
| 5,484,418 A | 1/1996 | Quiachon et al. | 604/167 |
| 5,484,424 A * | 1/1996 | Cottenceau et al. | 604/282 |
| 5,507,767 A | 4/1996 | Maeda et al. | 606/198 |
| 5,512,044 A | 4/1996 | Duer | 604/22 |
| 5,527,354 A | 6/1996 | Fontaine et al. | 623/1 |
| 5,536,242 A | 7/1996 | Willard et al. | 604/30 |
| 5,540,707 A | 7/1996 | Ressemann et al. | 606/159 |
| 5,549,626 A | 8/1996 | Miller et al. | 606/200 |
| 5,562,724 A | 10/1996 | Vorwerk et al. | 623/1 |
| 5,569,274 A | 10/1996 | Rapacki et al. | 606/158 |
| 5,569,275 A | 10/1996 | Kotula et al. | 606/159 |
| 5,634,897 A | 6/1997 | Dance et al. | 604/35 |
| 5,658,296 A | 8/1997 | Bates et al. | 606/127 |
| 5,662,671 A | 9/1997 | Barbut et al. | 606/170 |
| 5,669,933 A | 9/1997 | Simon et al. | 600/200 |
| 5,695,519 A | 12/1997 | Summers et al. | 606/200 |
| 5,709,704 A | 1/1998 | Nott et al. | 606/200 |
| 5,720,764 A | 2/1998 | Naderlinger | 606/200 |
| 5,728,066 A | 3/1998 | Daneshvar | 604/96 |
| 5,746,758 A | 5/1998 | Nordgren et al. | 606/159 |
| 5,749,848 A | 5/1998 | Jang et al. | 604/53 |
| 5,769,816 A | 6/1998 | Barbut et al. | 604/96 |
| 5,779,716 A | 7/1998 | Cano et al. | 606/114 |
| 5,792,157 A | 8/1998 | Mische et al. | |
| 5,792,300 A | 8/1998 | Inderbitzen et al. | 156/244.13 |
| 5,795,322 A | 8/1998 | Boudewijn | 604/22 |
| 5,797,952 A | 8/1998 | Klein | 606/198 |
| 5,800,457 A | 9/1998 | Gelbfish | 606/200 |
| 5,800,525 A | 9/1998 | Bachinski et al. | 623/1 |
| 5,810,874 A | 9/1998 | Lefebvre | 606/200 |
| 5,814,064 A | 9/1998 | Daniel et al. | 606/200 |
| 5,817,102 A | 10/1998 | Johnson et al. | 606/108 |
| 5,827,324 A | 10/1998 | Cassell et al. | 606/200 |
| 5,833,644 A | 11/1998 | Zadno-Azizi et al. | 604/52 |
| 5,833,650 A | 11/1998 | Imran | 604/53 |
| 5,846,260 A | 12/1998 | Maahs | 606/200 |
| 5,848,964 A | 12/1998 | Samuels | 600/200 |
| 5,876,367 A | 3/1999 | Kaganov et al. | 604/8 |
| 5,893,867 A | 4/1999 | Bagaoisan et al. | 606/198 |
| 5,893,869 A | 4/1999 | Barnhart et al. | |
| 5,895,399 A | 4/1999 | Barbut et al. | 606/159 |

| Patent Number | Date | Inventor | Class |
|---|---|---|---|
| 5,902,263 A | 5/1999 | Patterson et al. | 604/22 |
| 5,906,618 A | 5/1999 | Larson, III | 606/108 |
| 5,908,435 A | 6/1999 | Samuels | 606/200 |
| 5,910,154 A | 6/1999 | Tsugita et al. | 606/200 |
| 5,911,734 A | 6/1999 | Tsugita et al. | 606/200 |
| 5,916,193 A | 6/1999 | Stevens et al. | 604/53 |
| 5,925,016 A | 7/1999 | Chornenky et al. | 604/96 |
| 5,925,060 A | 7/1999 | Forber | 606/191 |
| 5,925,062 A | 7/1999 | Purdy | 606/200 |
| 5,925,063 A | 7/1999 | Khosravi | 606/200 |
| 5,928,203 A | 7/1999 | Davey et al. | 604/247 |
| 5,928,218 A | 7/1999 | Gelbfish | 604/540 |
| 5,934,284 A | 8/1999 | Plaia et al. | 128/898 |
| 5,935,139 A | 8/1999 | Bates | 606/159 |
| 5,938,645 A | 8/1999 | Gordon | 604/264 |
| 5,941,869 A | 8/1999 | Patterson et al. | 604/508 |
| 5,941,896 A | 8/1999 | Kerr | 606/200 |
| 5,947,995 A | 9/1999 | Samuels | 606/200 |
| 5,951,585 A | 9/1999 | Cathcart et al. | 606/198 |
| 5,954,745 A | 9/1999 | Gertler et al. | 606/200 |
| 5,976,153 A * | 11/1999 | Fischell et al. | 606/108 |
| 5,976,172 A | 11/1999 | Homsma et al. | 606/200 |
| 5,980,555 A | 11/1999 | Barbut et al. | |
| 5,989,210 A | 11/1999 | Morris et al. | 604/22 |
| 5,989,271 A | 11/1999 | Bonnette et al. | 606/159 |
| 5,989,281 A | 11/1999 | Barbut et al. | 606/200 |
| 5,993,469 A | 11/1999 | McKenzie et al. | 606/159 |
| 5,997,557 A | 12/1999 | Barbut et al. | 606/159 |
| 6,001,118 A | 12/1999 | Daniel et al. | 606/200 |
| 6,007,557 A | 12/1999 | Ambrisco et al. | 606/200 |
| 6,010,522 A | 1/2000 | Barbut et al. | 606/200 |
| 6,013,085 A | 1/2000 | Howard | 606/108 |
| 6,027,520 A | 2/2000 | Tsugita et al. | 606/200 |
| 6,042,598 A | 3/2000 | Tsugita et al. | |
| 6,051,014 A | 4/2000 | Jang | 606/200 |
| 6,051,015 A | 4/2000 | Maahs | |
| 6,053,932 A | 4/2000 | Daniel et al. | 606/200 |
| 6,059,814 A | 5/2000 | Ladd | 606/200 |
| 6,066,149 A | 5/2000 | Samson et al. | |
| 6,068,645 A | 5/2000 | Tu | 606/200 |
| 6,086,605 A | 7/2000 | Barbut et al. | 606/200 |
| 6,117,154 A | 9/2000 | Barbut et al. | |
| 6,129,739 A | 10/2000 | Khosravi | 606/200 |
| 6,136,016 A | 10/2000 | Barbut et al. | |
| 6,142,987 A | 11/2000 | Tsugita | 604/500 |
| 6,152,946 A | 11/2000 | Broome et al. | 606/200 |
| 6,165,200 A | 12/2000 | Tsugita et al. | 606/200 |
| 6,168,579 B1 | 1/2001 | Tsugita | 604/96.01 |
| 6,171,327 B1 | 1/2001 | Daniel et al. | 606/200 |
| 6,171,328 B1 | 1/2001 | Addis | |
| 6,179,851 B1 | 1/2001 | Barbut et al. | 606/159 |
| 6,179,859 B1 | 1/2001 | Bates et al. | 606/200 |
| 6,179,861 B1 | 1/2001 | Khosravi et al. | 606/200 |
| 6,203,561 B1 | 3/2001 | Ramee et al. | 606/200 |
| 6,206,868 B1 | 3/2001 | Parodi | |
| 6,214,026 B1 | 4/2001 | Lepak et al. | 606/200 |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,244 B2 * | 11/2001 | Suresh et al. | 604/525 |
| 6,319,268 B1 | 11/2001 | Ambrisco et al. | |
| 6,344,049 B1 | 2/2002 | Levinson et al. | |

FOREIGN PATENT DOCUMENTS

| | | | |
|---|---|---|---|
| EP | 0 472 368 A2 | 2/1992 | A61B/17/22 |
| EP | 0 522 735 A | 1/1993 | |
| EP | 0 533 511 A1 | 3/1993 | A61M/29/02 |
| EP | 0 655 228 A1 | 11/1994 | A61F/2/02 |
| EP | 0 686 379 A2 | 6/1995 | A61F/2/06 |
| EP | 0 696 447 A2 | 2/1996 | A61F/2/06 |
| EP | 0 737 450 A1 | 10/1996 | A61F/2/01 |
| EP | 0 743 046 A1 | 11/1996 | A61F/2/01 |
| EP | 0 759 287 A1 | 2/1997 | A61F/2/01 |
| EP | 0 761 250 A | 3/1997 | |
| EP | 0 771 549 A2 | 5/1997 | A61F/2/01 |
| EP | 0 784 988 A1 | 7/1997 | A61M/5/165 |
| EP | 0 852 132 A1 | 7/1998 | A61F/2/01 |
| EP | 0 934 729 | 8/1999 | A61B/17/22 |
| EP | 1 127 556 A2 | 8/2001 | |
| FR | 2 580 504 | 10/1986 | A61M/1/00 |
| FR | 2 643 250 A1 | 8/1990 | A61B/17/00 |
| FR | 2 666 980 | 3/1992 | A61F/2/02 |
| FR | 2 694 687 | 8/1992 | |
| FR | 2 768 326 A1 | 3/1999 | A61F/2/01 |
| GB | 2 020 557 B | 1/1983 | A61B/17/50 |
| JP | 8-187294 A | 7/1996 | A61M/29/00 |
| SU | 764684 | 9/1980 | A61M/25/00 |
| WO | WO 92/03097 | 3/1992 | A61B/17/00 |
| WO | WO 94/14389 | 7/1994 | A61F/2/02 |
| WO | WO 94/24946 | 11/1994 | A61B/17/22 |
| WO | WO 96/01591 | 1/1996 | A61B/17/22 |
| WO | WO 96/10375 | 4/1996 | A61F/2/06 |
| WO | WO 96/19941 | 7/1996 | A61B/17/00 |
| WO | WO 96/23441 | 8/1996 | A61B/5/00 |
| WO | WO 96/33677 | 10/1996 | A61F/11/00 |
| WO | WO 97/17100 | 5/1997 | A61M/29/00 |
| WO | WO 97/27808 | 8/1997 | A61B/17/22 |
| WO | WO 97/42879 | 11/1997 | A61B/17/00 |
| WO | WO 98/02084 | 1/1998 | |
| WO | WO 98/02112 | 1/1998 | A61F/2/01 |
| WO | WO 98/23322 | 6/1998 | A61M/29/00 |
| WO | WO 98/33443 | 8/1998 | A61B/17/22 |
| WO | WO 98/34673 | 8/1998 | A61M/31/00 |
| WO | WO 98/36786 | 8/1998 | A61M/5/32 |
| WO | WO 98/38920 | 9/1998 | A61B/17/00 |
| WO | WO 98/38929 | 9/1998 | A61B/17/22 |
| WO | WO 98/39046 | 9/1998 | A61M/25/00 |
| WO | WO 98/39053 | 9/1998 | A61M/29/00 |
| WO | WO 98/46297 | 10/1998 | A61M/29/00 |
| WO | WO 98/47447 | 10/1998 | A61F/2/06 |
| WO | WO 98/49952 | 11/1998 | A61B/17/32 |
| WO | WO 98/50103 | 11/1998 | A61M/29/00 |
| WO | WO 98/51237 | 11/1998 | A61F/2/01 |
| WO | WO 98/55175 | 12/1998 | A61M/29/00 |
| WO | WO 99/09895 | 3/1999 | A61B/17/12 |
| WO | WO 99/22673 | 5/1999 | A61F/2/01 |
| WO | WO 99/23976 | 5/1999 | A61F/2/01 |
| WO | WO 99/25252 | 5/1999 | A61B/17/00 |
| WO | WO 99/30766 | 6/1999 | A61M/29/00 |
| WO | WO 99/40964 | 8/1999 | A61M/29/02 |
| WO | WO 99/42059 | 8/1999 | A61F/2/06 |
| WO | WO 99/44510 | 9/1999 | A61B/17/00 |
| WO | WO 99/44542 | 9/1999 | A61F/2/06 |
| WO | WO 99/55236 | 11/1999 | A61B/17/00 |
| WO | WO 99/58068 | 11/1999 | A61B/17/22 |
| WO | WO 00/07521 | 2/2000 | |

| | | | |
|---|---|---|---|
| WO | WO 00/07655 | 2/2000 | .......... A61M/29/00 |
| WO | WO 00/09054 | 2/2000 | ............. A61F/7/12 |
| WO | WO 00/16705 | 3/2000 | ........... A61B/17/22 |
| WO | WO 00/49970 | 8/2000 | ............. A61F/2/01 |
| WO | WO 00/53120 | 9/2000 | |
| WO | WO 00/67664 | 11/2000 | |
| WO | WO 00/67665 | 11/2000 | |
| WO | WO 00/67666 | 11/2000 | |
| WO | WO 00/67668 | 11/2000 | |
| WO | WO 00/67669 | 11/2000 | |
| WO | WO 01/05462 | 1/2001 | |
| WO | WO 01/08595 | 2/2001 | |
| WO | WO 01/08596 | 2/2001 | |
| WO | WO 01/08742 | 2/2001 | |
| WO | WO 01/08743 | 2/2001 | |
| WO | WO 01/10320 | 2/2001 | |
| WO | WO 01/15629 | 3/2001 | |
| WO | WO 01/21077 | 3/2001 | |
| WO | WO 01/21100 | 3/2001 | |
| WO | WO 01/26726 | 4/2001 | |
| WO | WO 01/35857 | 5/2001 | |
| WO | WO 01/43662 | 6/2001 | |
| WO | WO 01/47579 | 7/2001 | |
| WO | WO 01/49208 | 7/2001 | |
| WO | WO 01/49209 | 7/2001 | |
| WO | WO 01/49215 | 7/2001 | |
| WO | WO 01/49355 | 7/2001 | |
| WO | WO 01/52768 | 7/2001 | |
| WO | WO 01/58382 | 8/2001 | |
| WO | WO 01/60442 | 8/2001 | |
| WO | WO 01/67989 | 9/2001 | |
| WO | WO 01/70326 | 9/2001 | |
| WO | WO 01/72205 | 10/2001 | |
| WO | WO 01/87183 | 11/2001 | |
| WO | WO 01/89413 | 11/2001 | |
| WO | WO 01/91824 | 12/2001 | |

OTHER PUBLICATIONS

"Endovascular Grafts, Stents Drive Interventional Radiology Growth," *Cardiovascular Device Update*, 2(3):1–12 (Mar. 1996).

"Protruding Atheromas in the Thoracic Aortic and Systemic Embolization," pp. 423–427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601–604 (Sep. 1983).

Cragg, Andrew et al., "Nonsurgical Placement of Arterial Endoprosthesis: A New Technique Using Nitinol Wire," *AJR*, pp. 261–263 (Apr. 1983).

Diethrich et al., "Percutaneous Techniques for Endoluminal Carotid Interventions," *J. Endovasc. Surg.*, 3:182–202 (1996).

Fadali, A. Moneim, "A filtering device for the prevention of particulate embolization during the course of cardiac surgery," *Surgery*, 64(3):634–639 (Sep. 1968).

Haissaguerre et al., "Spontaneous Initiation of Atrial Fibrillation by Ectopic Beats Originating in the Pulmonary Veins," *The New England Journal of Medicine*, 339(10):659–666 (Sep. 1988).

Jordan, Jr. et al., "Microemboli Detected by Transcranial Doppler Monitoring . . . ," *Cardiovascular Surgery*, 7(1)33–38 (Jan. 1999).

Lesh, "Can Catheter Ablation Cure Atrial Fibrillation?" *ACC Current Journal Review*, pp. 38–40 (Sep./Oct. 1997).

Lund et al., "Long–Term Patentcy of Ductus Arteriosus After Balloon Dilation: an Experimental Study," *Laboratory Investigation*, 69(4):772–774 (Apr. 1984).

Marache et al., "Percutaneous Transluminal Venous Angioplasty . . . ," *American Heart Journal*, 125(2 Pt 1):362–366 (Feb. 1993).

Mazur et al., "Directional Atherectomy with the Omnicath™: A Unique New Catheter System," *Catheterization and Cardiovascular Diagnosis*, 31:17–84 (1994).

Moussa, MD, Issaam "Stents Don't Require Systemic Anticoagulation . . . But the Technique (and Results) Must be Optimal," *Journal of Invasive Cardiol.*, 8(E):3E–7E, (1996).

Nakanishi et al., "Catheter Intervention to Venous Sytem Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386–392 (1998).

Theron et al., "New Triple Coaxial Catheter System for Carotid Angioplasty with Cerebral Protection," *American Journal of Neuroradiology*, 11:869–874 (1990).

Tunick et al., "Protruding atherosclerotic plaque in the aortic archo f patients with systemic embolization: A new finding seen by transesophageal echocardiography," *American Heart Journal* 120(3):658–660 (Sep. 1990).

Waksman et al., "Distal Embolization is Common After Directional Atherectomy . . . ," *American Heart Journal*, 129(3):430–435 (1995).

Wholey, Mark H. et al., PTA and Stents in the Treatment of Extracranial Circulation, *The Journal of Invasive Cardiology*, 8(E):25E–30E (1996).

* cited by examiner

VARIABLE WALL THICKNESS FOR DELIVERY SHEATH HOUSING

FIELD OF THE INVENTION

The present invention is related generally to medical devices. More specifically, the present invention includes tubular sheaths for delivering intravascular blood filtering devices.

BACKGROUND OF THE INVENTION

Blood vessels can become occluded in several ways. In one situation, a stenosis may be formed of an atheroma which can include a calcified material formed on the lumen walls of the blood vessel. In another situation, a stenosis can be formed of a thrombosis material which is typically softer than the calcified material, but can cause sudden and unpredictable blood flow reduction in a blood vessel lumen.

Different procedures have been developed to treat a stenotic lesion or stenosis in the vasculature. One method includes deforming the stenosis to reduce the restriction within the lumen of the blood vessel. This type of deformation is typically performed using balloon angioplasty. Another method includes the attempted removal of the stenosis or part of the stenosis. Removal of the stenotic lesion can be attempted through use of atherectomy, which can include mechanical ablation, radio frequency energy removal, and laser removal. In these methods, the stenosis can be mechanically cut or ablated from the vessel.

Problems may be encountered by the treating physician during thrombectomy and atherectomy. Stenotic debris, which may be separated from the stenosis, may be freed within the lumen of the vessel. If the debris flows distally, it can occlude distal vasculature and cause problems. If it flows proximally, it can enter the circulatory system which is also undesirable.

One technique for dealing with such debris includes filtering or otherwise removing the debris from within the vessel using an intravascular capture device. In one such method, a filtering device may be disposed distal of the stenosis during an atherectomy to catch the emboli or pieces of stenosis as they are released. These pieces or emboli may be removed using the capture device when the atherectomy procedure is complete. One such capture device includes a distal expandable filter member which can be placed distal of the stenosis to capture stenosis fragments. Expandable devices may be delivered through a delivery sheath and/or guide catheter to the treatment site. The delivery sheath and/or guide catheter may be retracted proximally prior to deploying the filter. After use, the filter may be retracted into the delivery sheath or guide catheter for removal.

What would be desirable are improved delivery sheaths for delivering distal protection devices to the treatment site. In particular, more benign delivery sheaths with distal ends that are easier to steer would be desirable.

SUMMARY OF THE INVENTION

The present invention includes delivery sheaths for intravascular emboli capturing filters, the sheath including an elongate tube having a distal region wall that is distally decreasing in thickness. In one embodiment, the distally decreasing wall thickness is imparted at least in part by a distally decreasing outside sheath diameter. In some embodiments, a tapered distal region forms a region of increasing softness relative to the more proximal adjacent region. One example of an expandable emboli filter is provided by U.S. Pat. No. 5,827,324, herein incorporated by reference.

The present invention includes intravascular emboli filtering systems including an elongate shaft having an expandable emboli filter operably coupled to the shaft distal region. The system can further include an elongate sheath region having a lumen therethrough for slidably accepting the expandable emboli filter in a collapsed state. The elongate sheath preferably has a tapered, distal region having a distally decreasing wall thickness. In one embodiment, the distally decreasing wall thickness is accomplished with a distally decreasing outside diameter. One embodiment includes a substantially sudden decrease in wall thickness at the distal region, rather than a gradual taper.

In use, the emboli filter may be collapsed, and disposed within the delivery sheath distal region. A guidewire may be advanced into the patient's vasculature and advanced further until the guidewire distal end is near the treatment site. In one method, the shaft of the emboli filter device serves as the guidewire. In another embodiment, a guidewire is first inserted, followed by the advancement of an emboli filter hollow shaft over the guidewire to a position distal of the treatment site. The emboli filter, in the collapsed state, within the delivery sheath, can be advanced together with the delivery sheath to a position near, and preferably distal of, the treatment site. The emboli filter may be advance distally out of the delivery sheath. In one method, the emboli filter is advanced distally, while the delivery sheath is held in substantially constant position. In another method, the emboli filter is held in substantially constant position, while the delivery sheath is proximally retracted.

The emboli filter, in an expanded configuration, may be left in place for the treatment process. The emboli filter may be used in conjunction with atherectomy or angioplasty procedures. After a procedure, the emboli filter may be collapsed, followed by retracting the emboli filter into the delivery sheath distal region. The emboli filter and delivery sheath may be retracted together and removed proximally from the patient's vasculature.

DETAILED DESCRIPTION OF THE INVENTION

Figure 1:
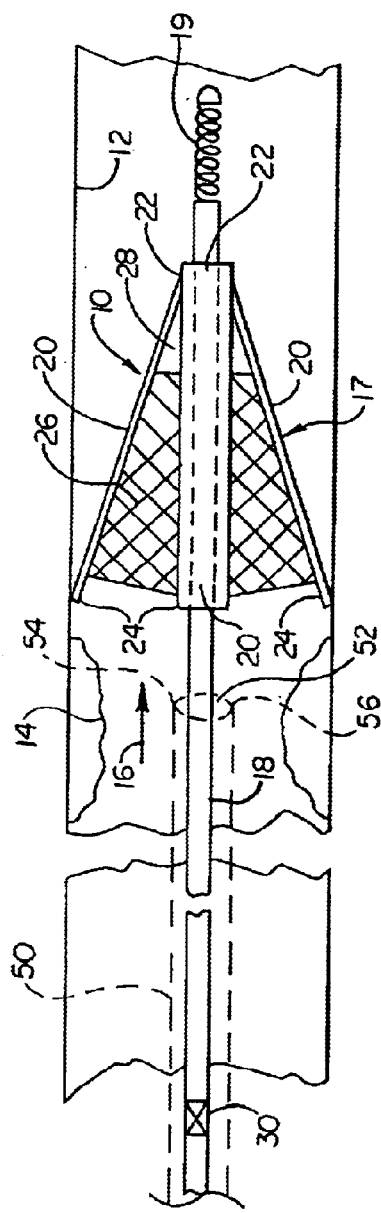
FIG. 1 is a longitudinal, cross-sectional view of a distal protection device within a vessel, shown in an expanded state, after advancement from within a delivery sheath.

FIG. 1 illustrates protection device 10 in a deployed, expanded position. Protection device 10 preferably includes a shaft or hollow guidewire 18, or a hypotube having the same general dimensions as a guidewire, having a coil tip 19, and a capturing assembly 17 which can include strut distal ends 22, strut proximal ends 24, a plurality of struts or wires 20, mesh 26 and inflatable member 28. The plurality of struts or wires 20 can be operably coupled to a distal region of shaft or hollow guidewire 18. The connection is preferably a hinge-type connection, so that the struts 20 have distal ends 22 coupled closely proximate the outer diameter of hollow guidewire 18 and proximal ends 24. When deployed, proximal ends 24 can be pivoted radially away from hollow guidewire 18. Mesh 26 is preferably formed of woven, knitted, or braided fibers or wires or other suitable filtering or netting-type material. Portions of mesh 26 can extend between struts 20. Inflatable member 28 is preferably coupled in fluid communication with an inner lumen which can run longitudinally within hollow guidewire 18.

Hollow guidewire 18 also preferably has a valve 30 coupled in a proximal portion thereof. During operation, a syringe is preferably connected to the proximal end of guidewire 18, which preferably includes a fluid-filled hypotube. The syringe is used to pressurize the fluid such that fluid is introduced through the lumen of hollow guidewire 18, through valve 30, and into inflatable member 28. Upon being inflated, inflatable member 28 preferably drives struts 20 to assume a deployed position in which ends 24 are pivotally or otherwise moved radially away from hollow guidewire 18 to a diameter which approximates the inner diameter of lumen 12. In this way, capturing assembly or filter 17 is deployed distally of stenosis 14 so that stenosis 14 can be severed and fragmented, and the fragments from stenosis 14 carried by blood flow, indicated by arrow 16, into the basket or chamber formed by the deployed filter 17. Filter 17 can then be collapsed and removed from vessel 12 with the fragments contained therein.

Figure 2:
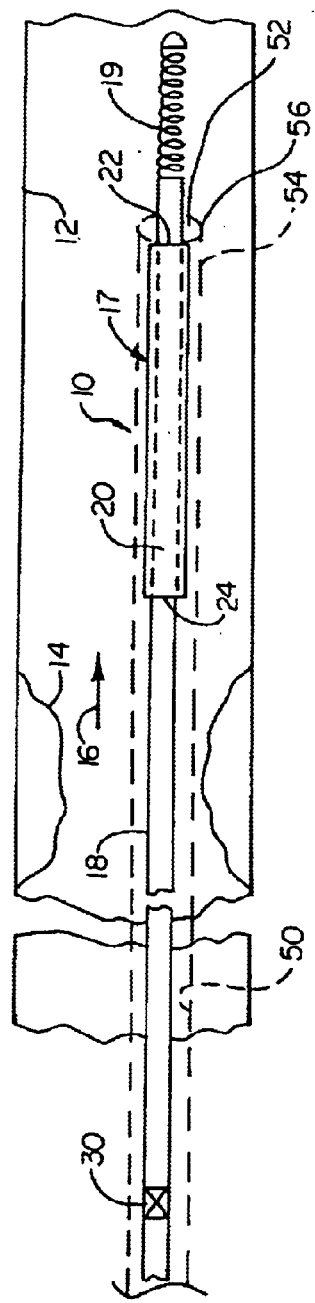
FIG. 2 is a longitudinal, cross-sectional view of the distal protection device of FIG. 1, shown in a collapsed state, after partial retraction within a delivery sheath.

A delivery sheath 50, illustrated in phantom in FIGS. 1 and 2, may be seen to be slidably disposed over guidewire 18 and be cooperatively sized so as to contain protection device 10 in a collapsed state. Delivery sheath 50 may be seen to have a distal region 54, a distal end 56, and has a lumen 52 therethrough. As illustrated in FIG. 1, protection device 10 has already been advanced from delivery sheath 50, and has been deployed.

FIG. 2 illustrates protection device 10 with filter 17 in the collapsed position. Items in FIG. 2 are similarly numbered to those shown in FIG. 1. FIG. 2 illustrates that mesh 26 is collapsible beneath struts 20. In order to collapse filter 17, fluid is preferably removed from inflatable member 28 through the lumen of hollow guidewire 18 and through two-way valve 30. This can be done using the syringe to pull a vacuum or using any other type of suitable fluid removal system.

Struts 20 are preferably formed of a resilient material which has some shape memory. Thus, when inflatable member 28 is collapsed, struts 20 can also collapse to approximate the outer diameter of hollow guidewire 18. In another preferred embodiment, struts 20 are fastened to inflatable member 28 through adhesive, or another suitable connector, so that they are effectively pulled to the collapsed position shown in FIG. 2 when the fluid is removed from inflatable member 28. In yet another preferred embodiment, inflatable member 28 is formed of a resilient, shape memory material. In that embodiment, inflatable member 28 is inflated by introducing fluid under pressure through the lumen in hollow guidewire 18, and into inflatable member 28. When pressure is released from the lumen in hollow guidewire 18, inflatable member 28 is allowed to force fluid out from the interior thereof through two-way valve 30 and to resume its initial collapsed position. Again, this can result in filter 17 assuming its collapsed position illustrated by FIG. 2. In FIG. 2, delivery sheath 50 may be seen to contain device 10, which has been collapsed. Delivery sheath 50 may be seen to entirely contain protection device 10.

Figure 3:
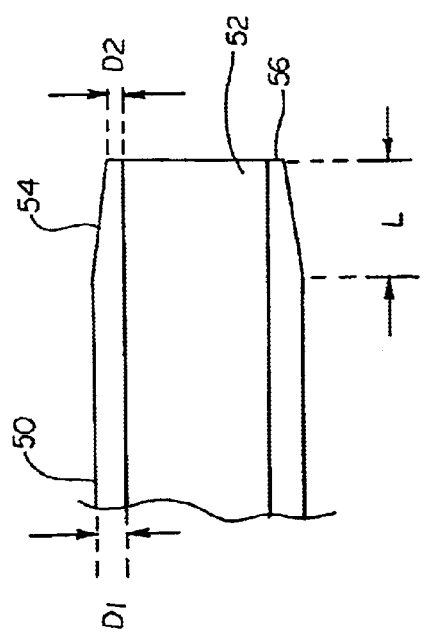
FIG. 3 is a longitudinal, cross-sectional view of a delivery sheath distal region.

FIG. 3 illustrates a side view of delivery sheath 50, including distal region 54 having a length indicated by "L".

As illustrated in FIG. 3, distal region 54 has a distally tapering wall thickness indicated by a proximal wall thickness "D1" and a smaller distal wall thickness indicated by "D2". In the embodiment illustrated, the distally tapering wall thickness is imparted by distally decreasing the outside diameter of the sheath. In some embodiments, the distally decreasing wall thickness imparts a distally increasing softness to the delivery sheath distal region. The delivery sheath tapering distal region length L is less than 10 millimeters in one embodiment, less than 5 millimeters in another embodiment, less than 2 millimeters in yet another embodiment, and is less than one millimeter in a preferred embodiment.

In one embodiment, proximal wall thickness D1 is about 0.002 inch, distal wall thickness D2 is about 0.001 inch, and distal region length L is about 1 millimeter. In one embodiment, not requiring separate illustration, the transition from proximal wall thickness D1 to distal wall thickness D2 is a substantially sudden step decrease, rather than a gradual taper.

Figure 4:
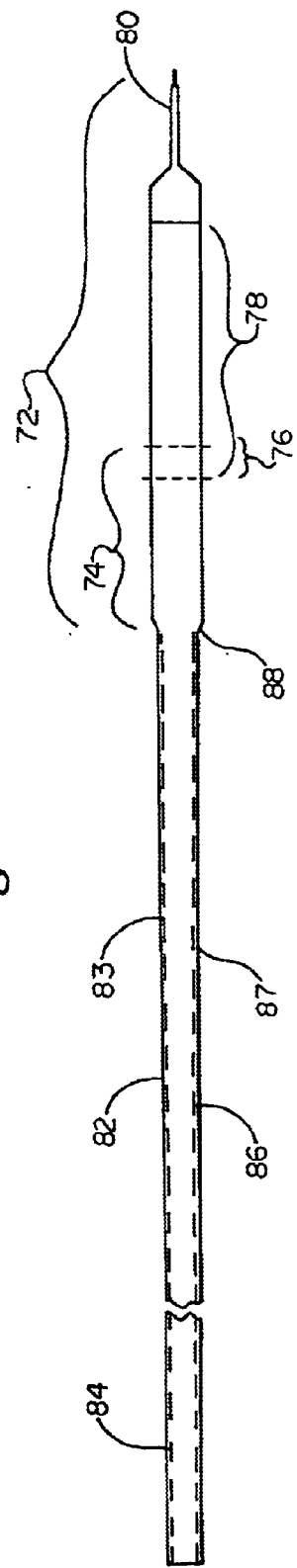
FIG. 4 is a side view of a delivery sheath in a process of manufacture.

FIG. 4 illustrates a delivery sheath 70. Delivery sheath 70 is shown in an intermediate stage of manufacture, prior to grinding and removal of a distal region of the sheath. Sheath 70 includes a sheath proximal region 84, a first intermediate region 82, a second intermediate region 83, followed by a distal portion 72. Distal portion 72 includes generally a distal region 74, a reduced diameter region 78, and a distal tip region 80.

In one embodiment, sheath proximal region 84 has an inside diameter of 0.0200 inch and a 0.0260-inch outside diameter, being expanded at a first flared region 86 to an outside diameter of 0.0290 inch in sheath first intermediate region 82. In this embodiment, sheath second intermediate region 83 has an outside diameter of 0.0310 inch increasing to an outside diameter of 0.0395 inch in sheath distal region 74 after an increase at a second flared region 88. In one embodiment, distal portion 72 has a wall thickness of 0.0022 inches in distal region 74, decreasing to a wall thickness of 0.0011 inch in sheath reduced diameter region 78 including far distal region 76. In one embodiment, sheath first intermediate region 82 has a length of about 0.100 inch, followed by sheath second intermediate region 83 having a length of about 0.25 inch, with sheath second intermediate region 83 and sheath distal region 74 together having a length of about 15 millimeter. In one embodiment, sheath far distal region 76 has a length of about 1 millimeter.

Sheath 70 can be manufactured by forming the intermediate stage substantially as illustrated in FIG. 4 from materials which can include polymeric materials such as polyether copolymers or nylons. Specifically, a tube can be formed having the aforementioned features and dimensions, including a closed distal tip region 80. The closed end tube can be ground using centerless grinding techniques well known in the art. Reduced diameter region 78 can be ground using the centerless grinding techniques until the wall thickness has been reduced relative to the proximal end of distal region 74. The sheath, after grinding, may be inserted into a mold and, using injection or blow molding techniques, the intermediate stage sheath may be molding to the desired shape. The molded sheath may then be removed from the mold, having the molded shape and further having reduced wall thickness distal region 78. The reduced wall thickness region 78 may then be partially removed by severing all but a small proximal region of the reduced diameter region, thus leaving the sheath with a small, reduced wall thickness distal region 76. In one embodiment, sheath far distal region 76 has been both reduced in wall thickness by grinding, and has had the more distal section severed, leaving sheath far distal region 76 as a remaining, short, reduced wall thickness region. In one embodiment, sheath far distal region 76 is a reduced wall thickness distal region having increased flexibility relative to the more proximal regions. The sheath formed by the centerless grinding, blow molding, and severing of the distal region may be ultimately used as a sheath for delivery and removal of an emboli filter.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. An elongate sheath configured to accommodate an intravascular emboli capturing device, the sheath comprising:

a proximal region having a distal end, the distal end having a first diameter;

an intermediate region having a proximal end and a distal end, the intermediate region increasing in diameter from its proximal end to its distal end; and a distal region having a proximal end and a distally tapering distal portion, the proximal end having a diameter that is greater than the diameter of the distal end of the intermediate region, the distally tapering distal portion tapering to a diameter that is less than the diameter of the proximal end of the distal region.

2. The elongate sheath of claim 1, wherein the sheath is configured to accommodate an intravascular emboli capturing device during device delivery.

3. The elongate sheath of claim 1, wherein the sheath is configured to accommodate an intravascular emboli capturing device during device retrieval.

4. The elongate sheath of claim 1, wherein the distally tapering distal portion of the distal region has a distally decreasing outer diameter.

5. The elongate sheath of claim 1, wherein the distally tapering distal portion of the distal region has a distally decreasing wall thickness.

\* \* \* \* \*